(12) United States Patent
Aoki et al.

(10) Patent No.: US 9,934,884 B2
(45) Date of Patent: Apr. 3, 2018

(54) CONNECTION PLATES FOR POWER FEEDING

(71) Applicant: Mitsubishi Electric Corporation, Chiyoda-ku, Tokyo (JP)

(72) Inventors: Ryusuke Aoki, Tokyo (JP); Jun Obata, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/324,494

(22) PCT Filed: Sep. 22, 2014

(86) PCT No.: PCT/JP2014/075061
§ 371 (c)(1),
(2) Date: Jan. 6, 2017

(87) PCT Pub. No.: WO2016/046881
PCT Pub. Date: Mar. 31, 2016

(65) Prior Publication Data
US 2017/0194072 A1    Jul. 6, 2017

(51) Int. Cl.
*H05H 9/00* (2006.01)
*H01B 5/02* (2006.01)
(Continued)

(52) U.S. Cl.
CPC .............. *H01B 5/02* (2013.01); *A61N 5/1042* (2013.01); *H01F 7/20* (2013.01); *H05H 7/04* (2013.01);
(Continued)

(58) Field of Classification Search
CPC .................................. H05H 13/04; H05H 9/00
(Continued)

(56) References Cited

U.S. PATENT DOCUMENTS 2,543,082 A * 2/1951 Webster ................... H05H 9/00
315/5.42
2,979,635 A * 4/1961 Burleigh .................. H05H 7/06
313/62
(Continued)

FOREIGN PATENT DOCUMENTS

JP        1-201905 A    8/1989
JP        7-176400 A    7/1995
(Continued)

OTHER PUBLICATIONS

International Search Report (PCT/ISA/210) issued on Dec. 16, 2014, by the Japanese Patent Office as the International Searching Authority for International Application No. PCT/JP2014/075061.

*Primary Examiner* — Alexander Talpalatski
(74) *Attorney, Agent, or Firm* — Buchanan Ingersoll & Rooney PC (57) ABSTRACT

Plural pairs of connection plates are placed circumferentially around a plurality of circularly-arranged electromagnets, in which the plural pairs are each a pair of two connection plates placed with a gap in a radial direction and are arranged in a longitudinal direction of the connection plates. At a portion where one of the two connection plates forming a pair and one of the adjacent two connection plates forming another pair are connected, an end portion of the one of the two connection plates forming the pair and an end portion of the one of the two connection plates forming the another pair, are configured to be bent in the radial direction so that these end portions are apart from the other one of the two connection plates forming the pair, whereby the connection plates in the pair and the connection plates in the another pair are serially connected.

4 Claims, 10 Drawing Sheets

(51) Int. Cl.
*H01F 7/20* (2006.01)
*H05H 7/04* (2006.01)
*H05H 13/04* (2006.01)
*A61N 5/10* (2006.01)

(52) U.S. Cl.
CPC ..... *H05H 13/04* (2013.01); *A61N 2005/1087* (2013.01); *H05H 2007/046* (2013.01)

(58) Field of Classification Search
USPC ....................................................... 315/5.42
See application file for complete search history.

(56) References Cited

U.S. PATENT DOCUMENTS

| | | | | |
|---|---|---|---|---|
| 3,067,359 A | * | 12/1962 | Pottier | H01J 17/04 313/363.1 |
| 3,328,708 A | * | 6/1967 | Smith | H05H 13/04 313/2.1 |
| 3,761,828 A | * | 9/1973 | Pollard | H05H 5/00 313/359.1 |
| 4,852,367 A | | 8/1989 | Dustmann | |
| 4,992,744 A | * | 2/1991 | Fujita | H05H 7/02 315/5.42 |
| 5,661,366 A | | 8/1997 | Hirota et al. | |
| 5,698,954 A | * | 12/1997 | Hirota | H05H 7/02 315/5.42 |
| 2007/0182498 A1 | | 8/2007 | Zumoto et al. | |

FOREIGN PATENT DOCUMENTS

| | | |
|---|---|---|
| JP | 11-144898 A | 5/1999 |
| JP | 2003-340400 A | 12/2000 |
| JP | 2002-008900 A | 1/2002 |
| JP | 2007-207706 A | 8/2007 |

\* cited by examiner

CONNECTION PLATES FOR POWER FEEDING

TECHNICAL FIELD

The present invention relates to connection plates used for feeding power to electromagnets in an accelerator or the like that is used, for example, in a research, medical or industrial field.

BACKGROUND ART

In a conventional accelerator, in order to connect a power source to electromagnets for every different type of electromagnet, cables are laid around the accelerator for every different type of electromagnet, and for example, a power source and deflection electromagnets are connected in parallel. Thus, such a number of cables proportional to the number of the deflection electromagnets are required, so that a large number of cables have to be used as a whole. Meanwhile, heretofore, there has been such a configuration in which power cables are used for serially connecting to each other the electromagnets of the accelerator or the like. In either of the above cases, cables are used for making connection between the power source and the electromagnets (see, for example, Patent Documents 1 and 2).

CITATION LIST

Patent Document

Patent Document 1: Japanese Patent Application Laid-open No. H07-176400 (FIG. 3)
Patent Document 2: Japanese Patent Application Laid-open No. 2000-340400 (FIG. 1)

SUMMARY OF THE INVENTION

Problems to be Solved by the Invention

Heretofore, at the time of the connection of the electromagnets, a configuration as described above is applied. Thus, at the work for connecting the power cables to the electromagnets at an actual place, in particular in the case where the electromagnets are large-sized ones that require a large electric current, it is required to lay a large number of power cables each having a large diameter. This makes the connection work troublesome at the time of laying the cables. Further, as an additional point, the power cable having a large diameter is not easily handleable itself, for example, it is difficult to be bent. Accordingly, there is a problem, for example, that the workload is very heavy, and thus the work is inefficient and uneconomical.

In addition, there is another problem, for example, that the installation place of the power cables is limited because they are to be laid on the ground, and their installed routes are largely limited in order to avoid their interference with the wirings of other devices or the pipe of cooling equipment.

This invention has been made to solve the problems as described above, and an object thereof is to provide connection plates which are used at the time of making connection to a plurality of electromagnets, in such a manner that power can be fed to the plurality of electromagnets by means of the plural connection plates, to thereby achieve work saving in the construction work at an actual place and effective utilization of a space for installation.

In this description, the connection plates each mean a plate for making electrical connection between an electromagnet and another electromagnet used in the accelerator, and as its material, a metal with superior electrical conductivity (for example, copper) is used.

Means for Solving the Problems

The connection plates for power feeding according to the invention are connection plates for power feeding which are placed at outer peripheral positions of a plurality of circularly-arranged electromagnets, each two of the connection plates forming a pair with a gap therebetween in a radial direction and plural pairs each being said pair arranged in a longitudinal direction of the connection plates;

wherein one of the connection plates in each one of the pairs is connected to one of the connection plates in adjacent another one of the pairs, at their ends in the longitudinal direction of the connection plates; and wherein an end portion of the other one of the connection plates in said each one of the pairs and an end portion of the other one of the connection plates in said another one of the pairs are bent in the radial direction so that these end portions are both apart from said one of the connection plates in said each one of the pairs, and said the other one of the connection plates in said each one of the pairs and said the other one of the connection plates in said another one of the pairs are serially connected to each other at their thus-bent portions, so that power is fed to the plurality of electromagnets.

Effect of the Invention

At the time of connecting the electromagnets such as those in the accelerator for accelerating the particle beam, to the power source, in the case of using plural connection plates, the electrically-conductive connection plates are serially connected to each other, so that, as compared to the case of using cables, it is possible to achieve reduction in the workload of the connection work, and thus the connection work can be performed efficiently. Further, it is possible to connect them with a smaller installation area, so that the cost for the installation can be suppressed.

MODES FOR CARRYING OUT THE INVENTION

Embodiment 1

Hereinafter, Embodiment 1 of the invention will be described based on the drawings.

Figure 1:
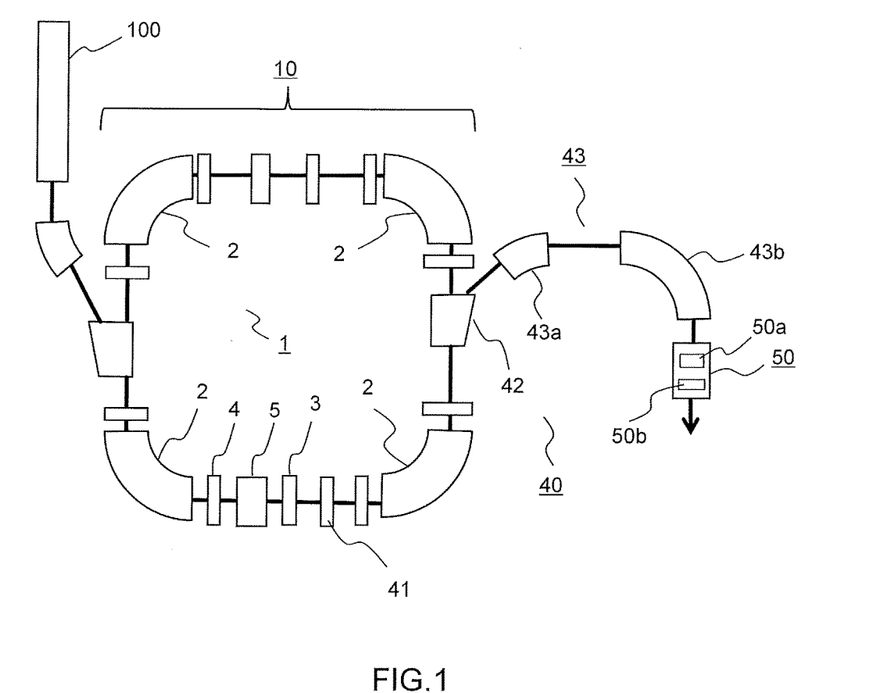
FIG. 1 is a plan view showing an example of an accelerator system including connection plates according to Embodiment 1 of the invention.

FIG. 1 shows a plan view of an apparatus using a synchrotron 1 that is an accelerator according to Embodiment 1, such as, a particle beam therapy apparatus or the like. A particle beam that is an aggregation of hydrogen ions (protons) or carbon ions generated by an ion source in an injector 100 is preliminarily accelerated up to a given energy using a linear accelerator in the injector 100. The preliminarily-accelerated particle beam is emitted from the injector and is then introduced into the synchrotron 1 while being deflected, being converged-diverged and being corrected in its trajectory, by a variety of electromagnets. In the synchrotron 1, a variety of electromagnets, such as deflection electromagnets 2, orbit-correction electromagnets 3, convergence/divergence electromagnets 4 and the like, are provided so that the particle beam circulates along a circulating orbit in the synchrotron 1 as an accelerator, and the particle beam repeatedly receives an acceleration electric field formed by a high-frequency acceleration cavity 5. In this case, because the particle beam is repeatedly accelerated by the acceleration electric field of the high-frequency acceleration cavity 5, its kinetic energy becomes higher at its every acceleration. As the kinetic energy becomes higher, an intensity of magnetic field required for deflection of the particle beam or the like, is changed. Thus, it is necessary to operate the variety of electromagnets 2 to 4 that constitute the synchrotron 1, and a high-frequency source and the like for providing the acceleration electric field in the high-frequency acceleration cavity 5, while temporally changing their operation parameters such as an applied current and the like, namely, to cause them to perform their respective patterned operations. The devices which are caused to perform such patterned operations are hereinafter referred to as an acceleration device group 10.

At the timing where the particle beam in the synchrotron 1 reaches a preset energy and thus the extraction of the particle beam becomes allowable, the acceleration device group 10 is operated in an emission-movement pattern, so that the particle beam is guided onto a trajectory for emission by an emission electrode 41. The moving direction of the particle beam on the trajectory for emission is deflected by an emission electromagnet 42, so that the particle beam is sent out to a particle beam transport section 43 outside the synchrotron. Here, the emission electrode 41 for guiding the particle beam to be emitted onto the trajectory for emission, and the emission electromagnet 42 for deflecting the moving direction of the particle beam from the trajectory for emission toward the particle beam transport section 43, are hereinafter referred to as an emission device group 40. Unlike the respective devices in the acceleration device group 10, the devices in such an emission device group 40 do not perform patterned operations, and are each set with a preset value corresponding to the energy of the particle beam to be emitted.

Further, the particle beam introduced into the particle beam transport section 43 is guided by other deflection electromagnets 43a, 43b and the like, to an apparatus outside the synchrotron 1, such as a particle beam therapy device 50 provided with a scanner 50a, a dose monitor 50b for measuring the dose, and the like, and is then put into use.

Figure 2:
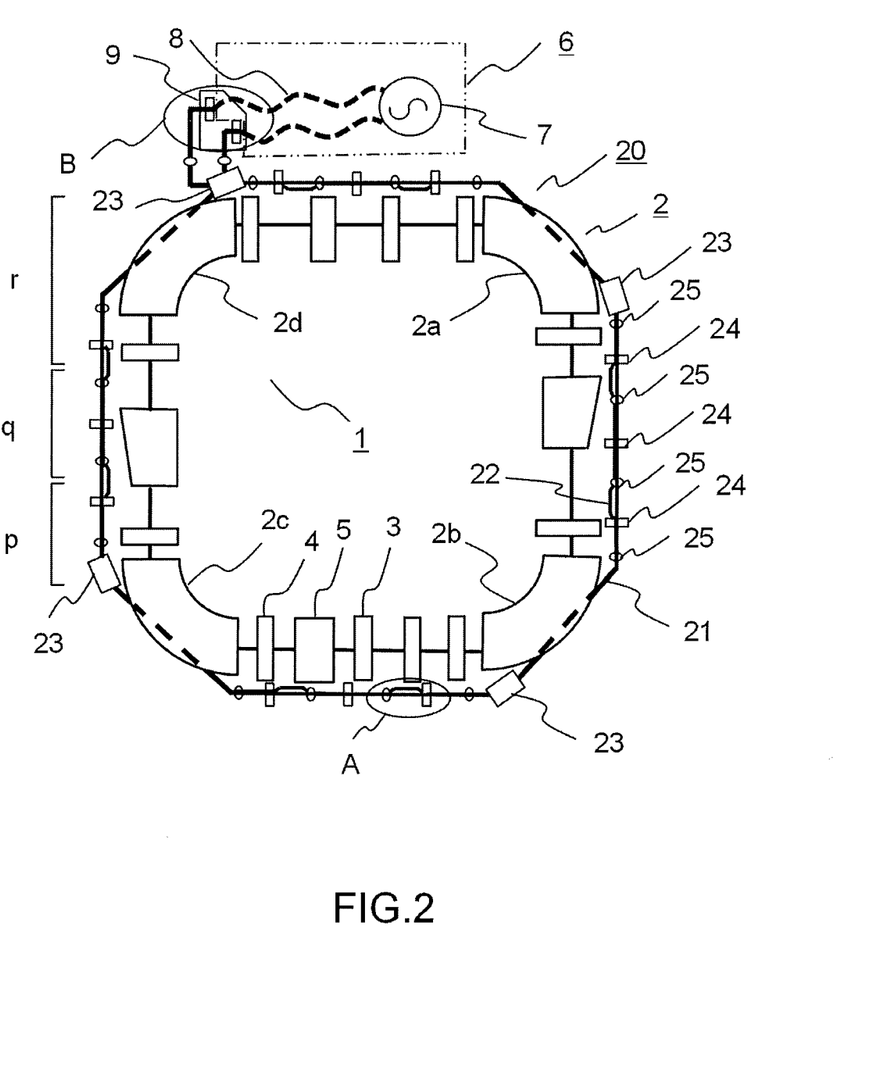
FIG. 2 is a plan view showing an example of an accelerator including the connection plates according to Embodiment 1 of the invention.

FIG. 2 is a plan view for illustrating configurations of the synchrotron 1 as an accelerator and a connection plate group 20 through which a current is applied to the variety of electromagnets 2 to 4 used in the accelerator. In this figure, the connection plate group 20 is configured with plural pairs of connection plates (referred also to as bus bars; the same applies hereinafter) 21 in which two of the connection plates form a pair as a unit, whose material is, for example, Cu, and which are arranged so as to surround the outer periphery of the variety of electromagnets that make the synchrotron 1 circular, in a form along the sides of a nearly octagonal shape. Note that, the connection plate group 20 is herein described as it is configured in a form along the sides of a nearly octagonal shape; however, the form is not necessarily along the sides of an octagonal shape so long as the connection plate group 20 is configured so as to surround the outer periphery of the variety of electromagnets, and thus the form may be along the sides of a polygonal shape other than an octagonal shape. Further, though not shown in the figure, the cooling equipment for cooling the variety of electromagnets is placed in the outer side of the periphery of the connection plate group 20, in a form similar to the above so as to surround the connection plate group 20.

Next, for describing the role of the connection plate group 20, description will be made in detail using FIG. 2. In order to apply a current to the variety of electromagnets, such as, the deflection electromagnets 2, the orbit-correction electromagnets 3, the convergence/divergence electromagnets 4 and the like in the synchrotron 1, the connection plates 21 of the connection plate group 20 are serially connected to the deflection electromagnets 2 and the like, from an electromagnet power source 7 that is a component of a current feeder 6, through cables 8 and a mutual-connection part 9 (Note that electromagnet power sources are individually placed for every different type of the electromagnet; however, in this figure, the electromagnet power source 7 connected to the deflection electromagnets 2 is illustrated as a representative thereof, and the other electromagnet power sources are omitted from illustration for simplification). Further, in consideration of easiness in assembling work, the connection plate group 20 is divided into the plural pairs of connection plates 21 in which two of the connection plates form a pair, and in order to configure them to be arranged in series in the longitudinal direction of the connection plates (the details will be described later), in the middle of the continuous sides of the octagonal shape, there are provided bent connection portions 22 for making connections at plural points and deflection-electromagnet connection parts 23 that are portions to be connected to the deflection electromagnets. Further, in order to prevent each of the connection plates 21 from being deflected by its own weight in their arranged track, there are provided pluralities of intermediate fixation plates 24 and clamping plates 25 for fixing and supporting the connection plates 21 at plural points in the middle. As aforementioned, in FIG. 2, with respect the connections between the variety of electromagnets and the connection plates, only the connections between the deflection electromagnets 2 that are the main electromagnets of the synchrotron 1 and the connection plates, are illustrated for simplification. Also in the case where a current is fed from a power source, using such connection plates, to the electromagnets other than the deflection electro-magnets 2, such as the orbit-correction electromagnets 3 and the convergence/divergence electromagnets 4, the configuration in which a current is fed from each electromagnet power source through its cables to each type of plural electromagnets, is similarly applied except only that operation parameters such as an applied current and the like are set differently. Note that the applied current and the like will be detailed later.

Figure 3:
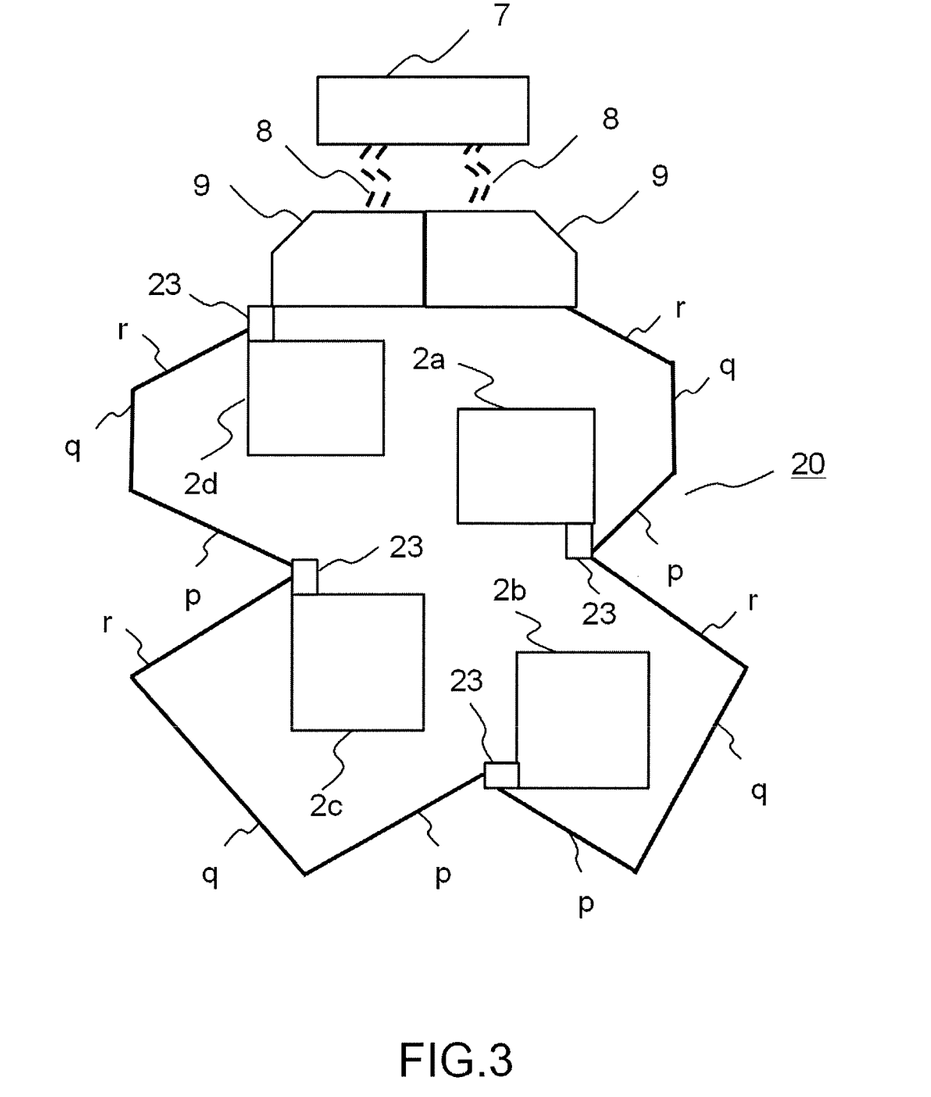
FIG. 3 is a diagram for illustrating a connection method of the connection plates according to Embodiment 1 of the invention.

Next, operations/functions of the connection plates 20 will be described using FIG. 3. FIG. 3 is a conceptual diagram for illustrating the case where, as the electromagnets of the synchrotron 1, the deflection electromagnets 2 that are typical electromagnets are focused on, and this electromagnets and the connection plate group 20 are connected to each other. Description will be made about the case of providing the thus-described configuration, as follows. In the figure, to the electromagnet power source 7, total four cables 8 are connected, two of which are provided in the output side (for example, in the right side) and the other two of which are provided in the input side, and these cables are further connected to the right and left deflection electromagnets 2 through the mutual-connection part 9. Although the deflection electromagnets 2 are configured with total four electromagnets as shown in FIG. 2, mutually adjacent deflection electromagnets in the four electromagnets are serially connected to each other at the deflection-electromagnet connection part 23 of each of the deflection electromagnets using respective pairs of connection plates shown at p, q, and r divided in the connection plate group 20. Accordingly, it is apparent that total 12 pairs of connection plates 21 are required.

Figure 10:
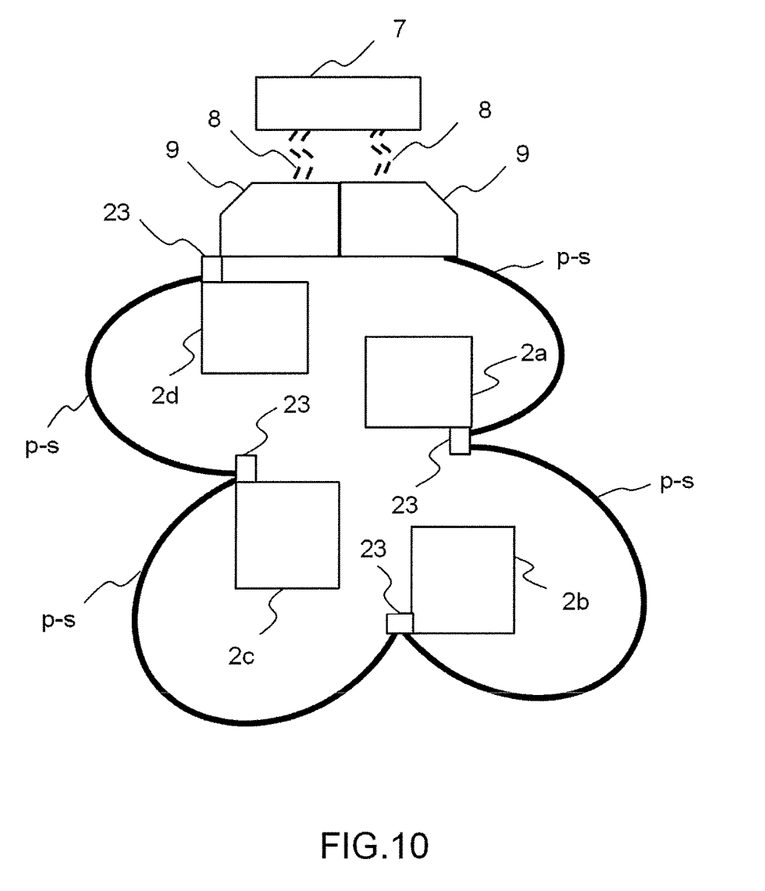
FIG. 10 is a conceptual diagram showing a commonly-used connection method between a power source and deflection electromagnets in an accelerator, in a case of using cables.

In contrast, according to the conventional system using cables, the required number of cables from the power source to the mutual-connection part 9 is totally four that is the same as in the case of using the connection plate group; however, as shown in FIG. 10, four cables are used between the mutual-connection part 9 and the deflection-electromagnet connection part 23 of each deflection electromagnet (in the figure, the indication p-s given at each of the curved portions by thick lines shows that the cable is not singly placed at each of the portions but the total four cables are used at each of the portions). This results in total 20 number of cables, so that the number is larger than the number of pairs of the connection plates. This is because, if a current is caused to flow in only one cable, the amount of the current having to flow becomes larger, so that a thicker cable is required and thus the workability is impaired significantly. Accordingly, as shown in this figure, the portion is configured with plural cables. In addition, because it is necessary to cause a large current in the order of 1000 amperes to flow in each of the deflection electromagnets 2, the size of each cable (a size that is represented, for example, by its diameter) becomes larger than the size of the connection plates [pair], even when total 20 number of cables are placed in the respective portions on every four-cable basis. As a result, the ground area necessary for installing these cables becomes, when converted into a ratio, 2 to 3 times the ground area in the case of using the connection plates. In other words, when the connection plates are used, the ground area necessary for installing the connection plates (an area necessary for installing only the connection plates), is just required to be equal to or less than half the area in the conventional case of using cables.

Figure 4:
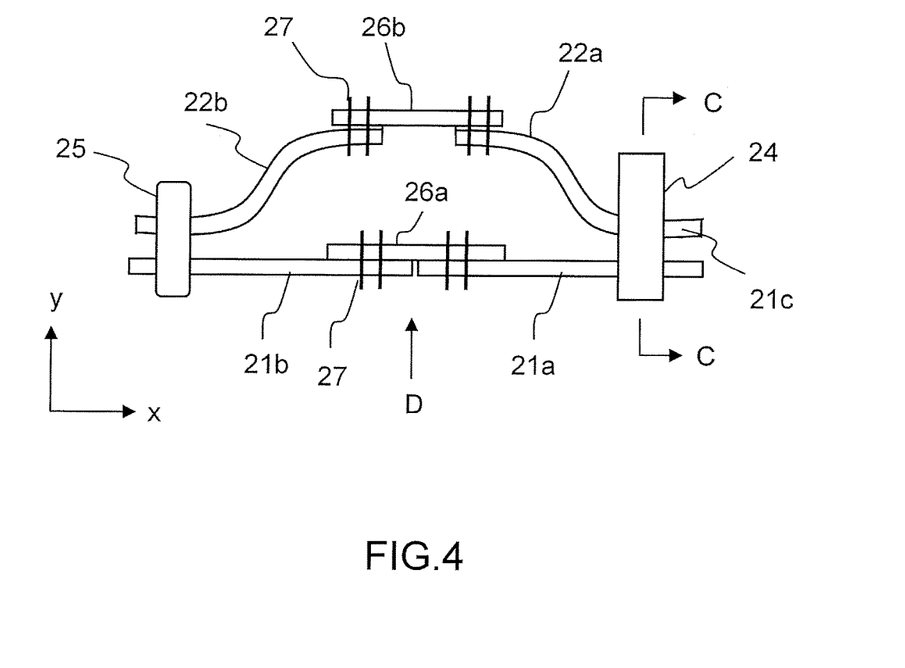
FIG. 4 is an enlarged view of a portion A (connection area) in FIG. 2.

In this respect, using FIG. 4, description will next be made about how to specifically install the connection plate group 20 comprising plural connection plates, around the respective electromagnets, also with description about a detailed structure around the connected portions between the connection plates 21 and between the bent connection portions 22. FIG. 4 is an enlarged view of a portion A (connection area) in FIG. 2. In order to make handling such as assembling work easier, the connection plate group 20 is configured as being divided into plural connection plates. FIG. 4 shows a plan-view configuration in each connection area where the plural connection plates are serially connected to each other. In the figure, two connection plates 21a and 21b are fixed and clamped, respectively, by the intermediate fixation plate 24 placed in the right-end side in the connection area and the clamping plate 25 placed in the left side therein, and are connected to each other in an x-direction (a longitudinal direction of the plate; the same applies hereinafter) using a joint plate 26a and screw fasteners 27. Likewise, two bent connection portions 22a and 22b are fixed and clamped, respectively, by the intermediate fixation plate 24 placed in the right-end side in the connection area and the clamping plate 25 placed in the left side therein, and are connected to each other in the x-direction using a joint plate 26b and screw fasteners 27. Note that each of the joint plates is not a constitutionally essential element, so that the two plates may be connected directly in a form overlapping each other. Further note that a y-direction is a radial direction with respect to the circularly-arranged positions of the variety of electromagnets that constitute the synchrotron 1 (the same applies hereinafter), and in this figure, the upper side corresponds to the inner peripheral side of the positions.

Between each two adjacent deflection electromagnets, there are provided three pairs of the connection plates, which are connected to each other at such a connected portion, in such a manner that the pairs are serially in contact with each other at the connected portion as a boundary (the pairs of the connection plates divided between the two adjacent deflection electromagnets 2c and 2d are representatively indicated by p, q, and r in FIG. 2; the same applies to the pairs between other adjacent two deflection electromagnets). Thus, total 3×4 pairs, namely, 12 pairs of connection plates are used.

In this manner, the bent connection portion 22 bent in an S-shape is partially provided in each of the connection plates in the connection area; this is intended to strengthen the connected state of the divided connection plates serially connected, and to make the work easier. Note that the reason why the bent connection portion 22 is provided by bending the inner-side connection portion in the connection portions of the two connection plates [pair], is to make the fastening work using the screw fasteners 27 easier even when the two connection plates are close to each other.

Figure 5:
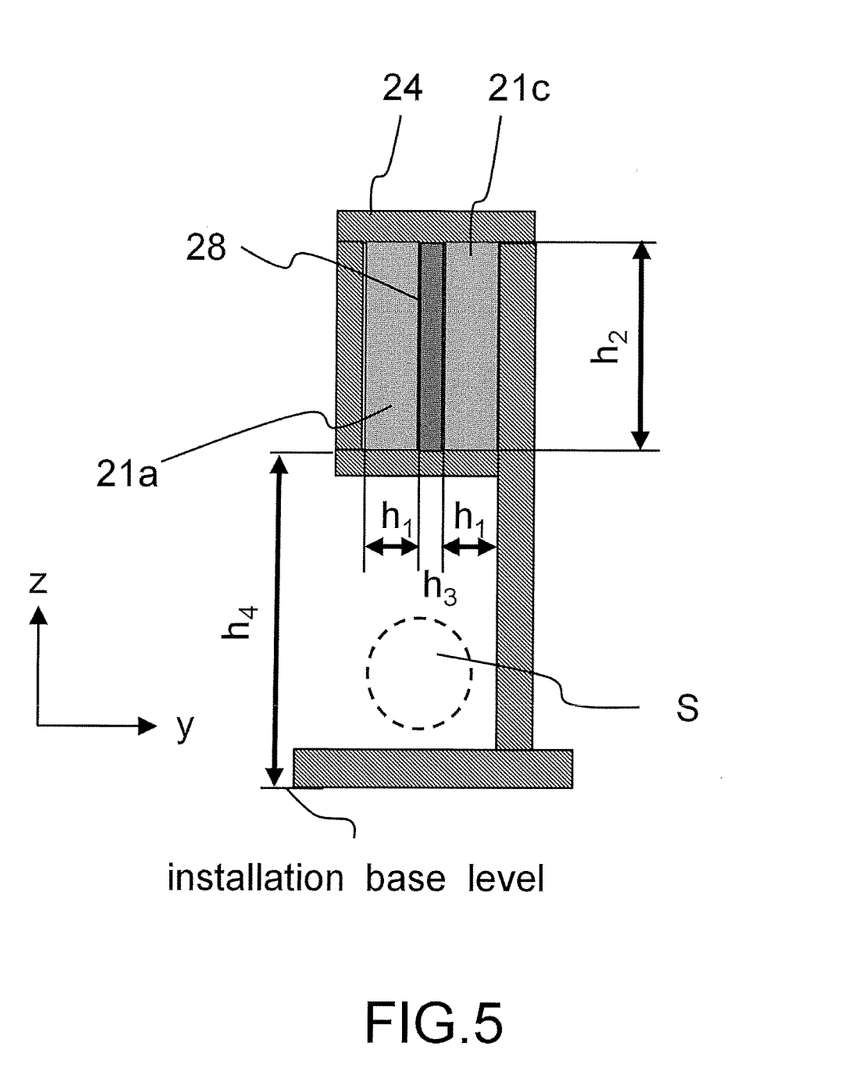
FIG. 5 is a diagram showing a CC cross-section in FIG. 4.

FIG. 5 is a diagram showing the CC cross-section in FIG. 4. The set of two-adjacent connection plates 21a, 21c each having a thickness of $h_1$ and a width of $h_2$ (this set of the two plates corresponds to each one of the pairs of the connection plates (corresponding to each one of p, q, r in FIG. 2)) are fixed by the intermediate fixation plate (material: glass epoxy laminate) 24 with a gap as an insulative space 28 therebetween established by an insulating member having a thickness of $h_3$ (material: glass epoxy laminate). In this figure, a z-direction is a width direction of the connection plate and corresponds to a height direction thereof (the same applies to the following figures). The thickness $h_1$ and the width $h_2$ of the connection plate are determined according to the allowable value of the current density of the current caused to flow in the connection plate. Further, the length L of the connection plate is set to a length of 1 m to 2 m (for example, with the thickness $h_1=10$ mm and the width $h_2=125$ mm) for the additional purpose of keeping its weight in a suitable range in order for the work at the assembling to proceed smoothly. When the intermediate fixation plate is used for fixing the connection plates in this manner, it is possible to reduce a deflected amount of the connection plate in the downward direction (in a direction opposite to the z-direction, that is, in the gravity direction) to about one-tenth as compared to the case without using the intermediate fixation plate.

Meanwhile, in general, the thickness $h_1$ of the connection plate, the thickness $h_3$ of the insulating plate [member] and the like, each have a value 0.01 times or less as compared to the outer peripheral size of the synchrotron 1, that is negligible. Thus, it can be said that, in a plane, the installation positions of the connection plates are placed nearly on the outer periphery of the synchrotron 1. Accordingly, if the cables are instead installed, whose outer diameter is two times or more the size of the connection plates (in particular, the size $(2h_1+h_3)$ in the thickness direction), the area required for their installation becomes much larger, in particular in the case where the cables are required to be installed on the ground outside the respective electromagnets of the synchrotron 1. In other words, when the connection plates are used, there is provided such an effect that, as compared to the case of using the cables, the required ground area can be reduced by the size of the cable.

Further, in general, these connection plates are placed on a position at a height of $h_4$ from the installation base level, so that an under space S is formed with the connection plates (or, the intermediate fixation plate). Thus, there is provided an effect that, as compared to the case of using the cables, the under space S can be utilized efficiently (for example, the space can be partly utilized as an installation space of the pipe of cooling equipment), in particular in the case, for example, where there is restriction in the ground area. Note that in the case of the cables, they are generally placed directly at the installation base level (for example, on the ground), so that the under space S is not provided.

Figure 6:
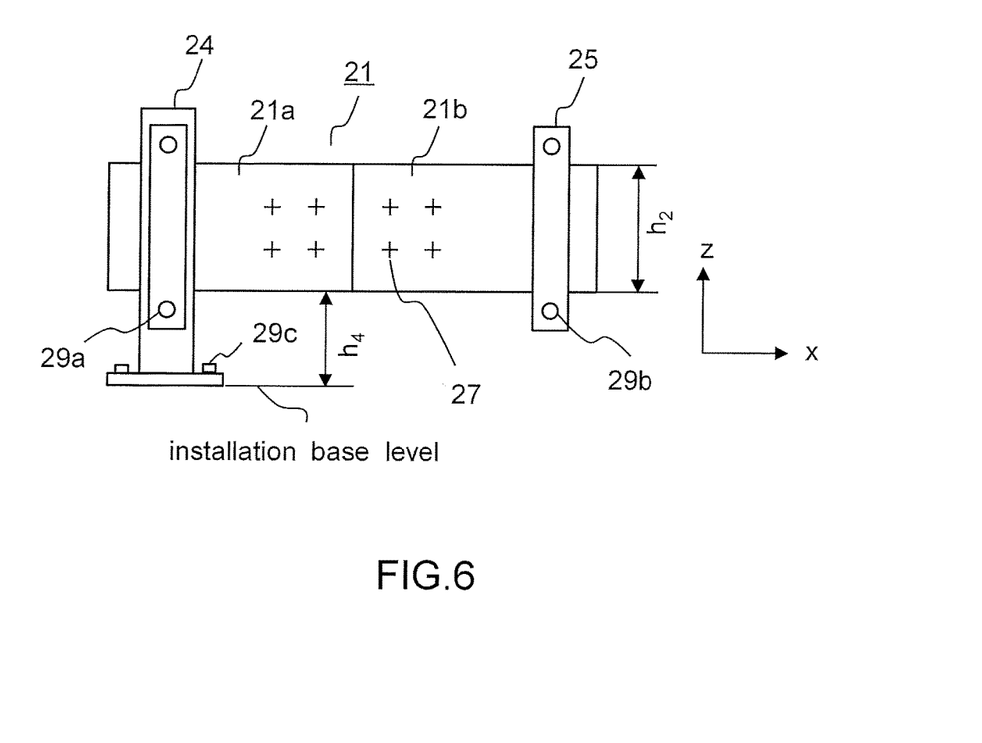
FIG. 6 is a diagram showing a view in a direction of arrow D in FIG. 4.

FIG. 6 is a diagram showing a view in a direction of arrow D in FIG. 4. The connection plates 21 each having the width $h_2$ (in detail, two connection plates 21a, 21b connected in series using the screw fasteners 27) are placed on the position at the height (installation base height; the same applies hereinafter) $h_4$ from the installation base level, in a manner fixed by the intermediate fixation plate 24 and clamped by the clamping plate 25. Indicated at 29a, 29b and 29c are fastening bolts.

Figure 7:
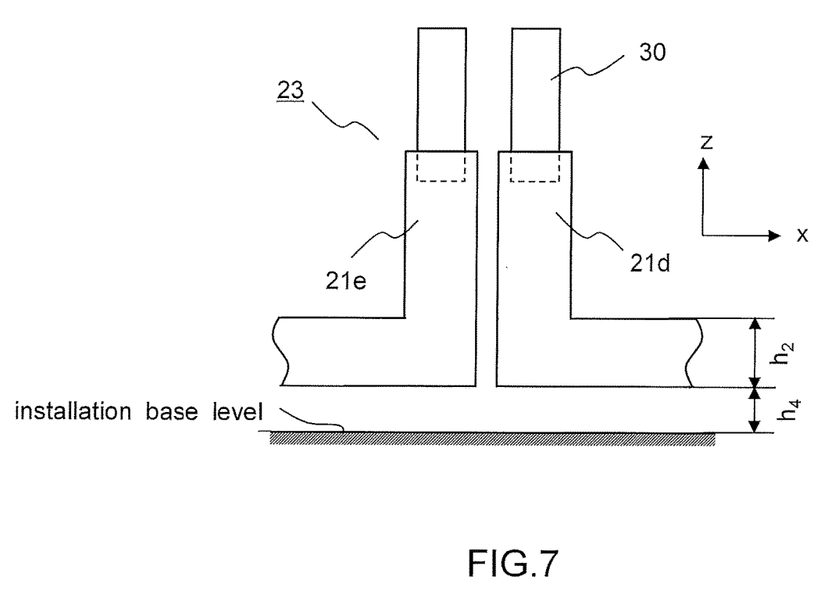
FIG. 7 is a partial enlarged view of a deflection-electromagnet connection part according to Embodiment 1 of the invention.

FIG. 7 is a partial enlarged view of the deflection-electromagnet connection part 23 in FIG. 2, in which a connected state between the connection plates 21 and connection ends 30 of the deflection electromagnet, for feeding a current to the deflection electromagnet, is schematically shown (actually, they are screw-fastened together using bolts and nuts). In general, electromagnets such as the deflection electromagnets 2 are placed on a position at a higher height ($>h_2+h_4$) than the height $h_4$ by a distance more than the width $h_2$ of the connection plate 21, from the installation base level, so that, at that portion, as shown in the figure, the connection plate is provided with a structure having an L-shape bent upward (in the z-direction in the figure) (see, connection plates 21d and 21e). The provision of such a shape makes easier the connection work of the connection plate for feeding a current to the deflection electromagnet. Note that, although the description is herein made citing the deflection electromagnet 2 as an example, this electromagnet is not limitative and a similar argument can of course be established for the orbit-correction electromagnet 3, the convergence/divergence electromagnet 4 and the like.

Figure 8:
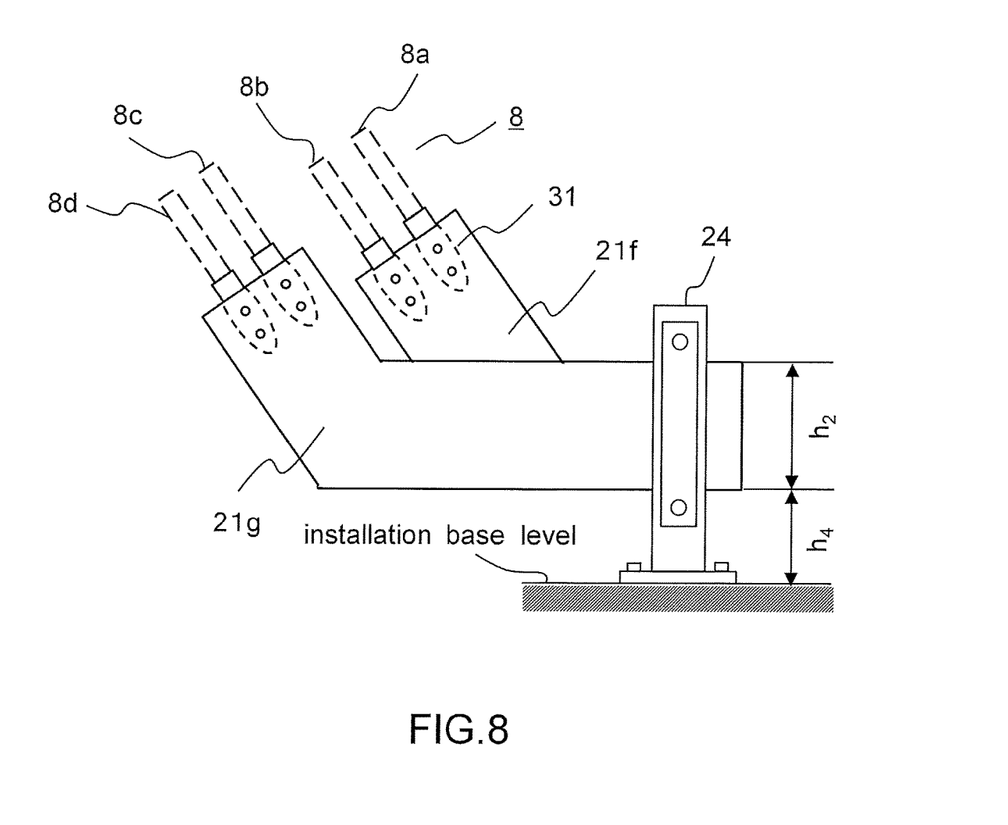
FIG. 8 is a partial enlarged view of a mutual-connection part between the connection plates and cables, according to Embodiment 1 of the invention.

Next, description will be made about the mutual-connection part 9 in a mutual-connection area indicated by the symbol B in FIG. 2. The mutual-connection part 9 is a portion where the cables 8 for feeding a current from the electromagnet power source 7 to the electromagnets and the connection plate group 20 described above are connected. In FIG. 8, a diagram around the portion where the cables 8 are connected is shown, that is a partial enlarged view of the mutual-connection part. In this figure, from the electromagnet power source 7, the cables 8 are divided into every two cables (see, 8a, 8b and 8c, 8d, in the figure), and are connected at their cable-ends to the respective two connection plates 21f and 21g fixed to the intermediate fixation plates 24, through the crimping terminals 31 (see the description of FIG. 3). Note that, on this occasion, the mounting position of each connection plate (target installation height) to the intermediate fixation plate 24 from the installation base level is $h_4$ that is the same as in the case of FIG. 5 to FIG. 7.

Consequently, as shown in FIG. 5 to FIG. 8, the mounting positions (heights) of the connection plates to the intermediate fixation plates 24 are made common as they are constantly at $h_4$, so that, in the installation work of them, when the mounting workers are going to mount the connection plates at specified positions using, for example, a crane or the like, it is easy to standardize the work, so that it becomes possible to enhance the efficiency of the installation work.

As described above, it can be understood that, in order to install the entire equipment of the synchrotron 1 with a smaller installation area, the system of using the connection plate group 20 is more advantageous than the conventional system using cables. Meanwhile, in order to operate the synchrotron 1, the aforementioned cooling equipment is required in addition to the connection plate group 20 that is current feeding equipment, so that a ground for the cooling equipment is further required. Even in that aspect, in consideration of the utilization of the under space S, it can be understood that the system of using the connection plate group 20 is more advantageous than the cable system.

Figure 9:
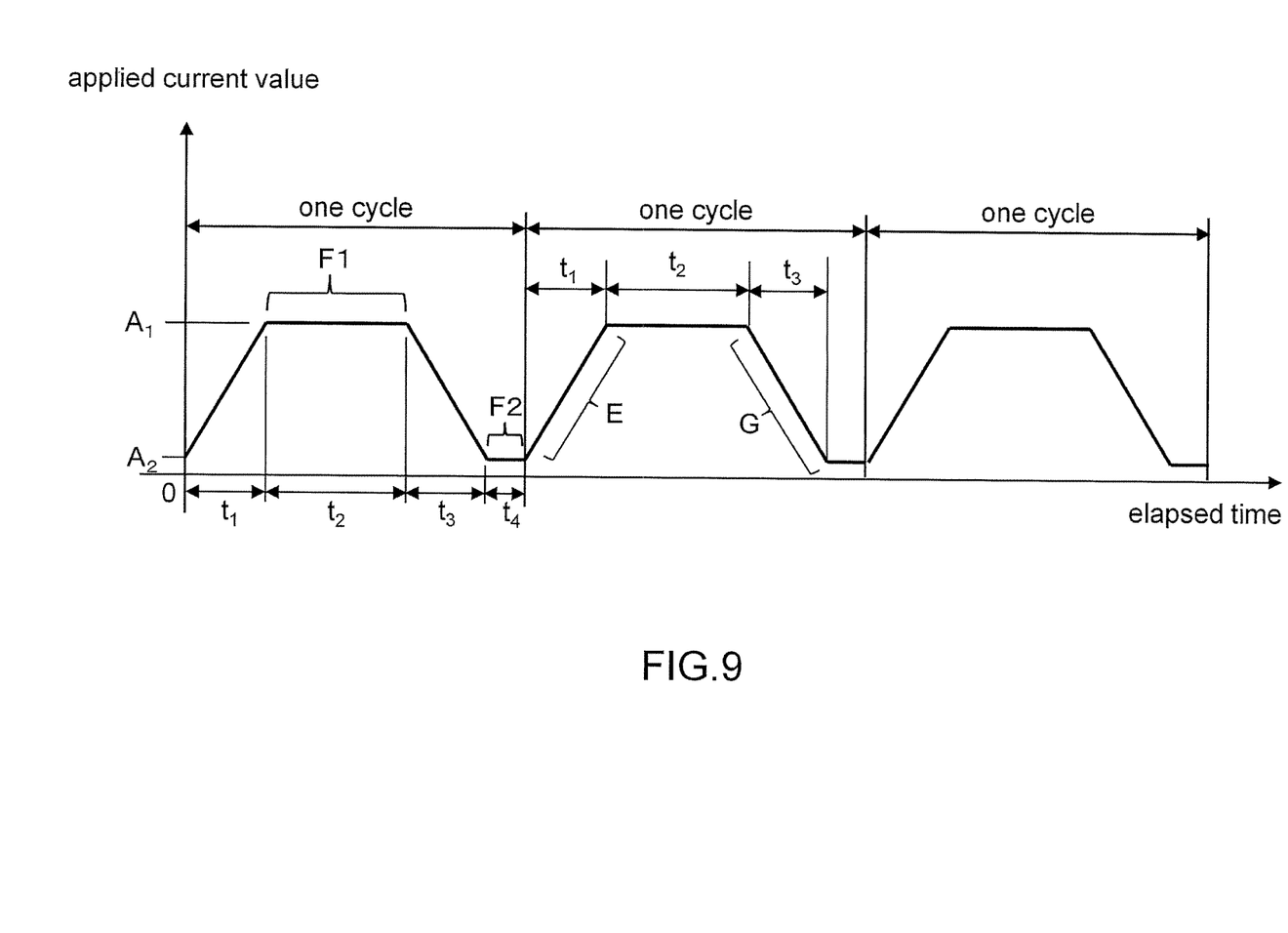
FIG. 9 is a diagram showing an example of a pattern of current that is applied to electromagnets by means of the connection plates according to Embodiment 1 of the invention.

Next, using FIG. 9, description will be made below about the operation parameter such as an applied current or the like that is one of factors for determining the shape of the connection plate. This figure is a schematic diagram showing an example of an operation pattern of a current caused to flow in the electromagnets such as deflection electromagnets, used in the synchrotron. Since the plurality of deflection electromagnets is installed as shown in FIG. 2, it is necessary to operate them in synchronization with each other at the time of accelerating protons or the like. For that reason, as shown in FIG. 9, as the pattern of the current applied to these electromagnets, such a pattern is used in which the current is patterned into a trapezoidal shape per one cycle.

In this figure, the ordinate represents an applied current value and the abscissa represents elapsed time. Further, the change amount per unit time of the current value in the current increasing section (the section indicated by a symbol E) shown by $t_1$ on the time axis, is the same as the change amount per unit time of the current value in the current decreasing section (the section indicated by a symbol G) shown by $t_3$ on the time axis. Further, the sections indicated by symbols F1, F2 (the sections shown respectively by $t_2$ and $t_4$ on the time axis) are sections where the respective current values are constant, and they are placed in a pattern in which a maximum current value $A_1$ is given in the section F1 and a minimum current value $A_2$ is given in the section F2. The reason why the section F2 is provided is because it is actually difficult to drastically change the current value from the section indicated by the symbol G (the negatively inclined section) directly to the section indicated by the symbol E (the positively inclined section), so that a flat section without current change such as the section F2 has to be provided.

In the above pattern, in the case of the deflection electromagnets, generally, the current value $A_1$ is set to the order of 1000 A and the current value $A_2$ is set to the order of one-tenth the above. Further, in the case of the convergence/divergence electromagnet 4 or the like, the maximum current value $A_1$ becomes a value that is smaller approximately by one order of magnitude than the above, and the minimum current value A2 is set to a value that is one-fourth the above or less. In this manner, the pattern of the applied current differs depending on a type of the electromagnet. Then, using an allowable current value per unit cross-section area, as a reference, that is determined according to such an applied current, the sizes of the connection plate, that is, $h_1$ and $h_2$, are determined. Namely, it is required to determine the sizes $h_1$ and $h_2$ of the connection plate so that the maximum current value $A_1$ is the allowable current value or less.

It should be noted that appropriate modification and omission in the embodiment may be made in the present invention without departing from the scope of the invention. For example, in the above description, such a case has been described as an example where the bent connection portion is placed in the inner side around the periphery of the synchrotron; however, this case is not limitative, and an effect similar to the above is accomplished in the case where the bent connection portion is placed in the outer side around the periphery of the synchrotron.

DESCRIPTION OF REFERENCE NUMERALS and SIGNS

1: synchrotron, 2, 2a, 2b, 2c, 2d: deflection electromagnet, 3: orbit-correction electromagnet, 4: convergence/divergence electromagnet, 5: high-frequency acceleration cavity, 6: current feeder, 7: electromagnet power source, 8: cables, 9: mutual-connection part, 20: connection plate group, 21, 21a, 21b, 21c, 21d, 21e, 21f, 21g: connection plate, 22, 22a, 22b: bent connection portion, 23: deflection-electromagnet connection part, 24: intermediate fixation plate, 25: clamping plate, 26: joint plate, 27: screw fastener, 30: connection end, A: connection area, B: mutual-connection area, $h_1$: thickness (of the connection plate), $h_2$: width (of the connection plate), $h_4$: height from the installation base level, L: length of the connection plate, x: longitudinal direction, y: radial direction, z: width direction.

The invention claimed is:

1. Connection plates for power feeding which are placed at outer peripheral positions of a plurality of circularly-arranged electromagnets, each two of the connection plates forming a pair with a gap therebetween in a radial direction and plural pairs each being said pair arranged in a longitudinal direction of the connection plates;
   wherein one of the connection plates in each one of the pairs is connected to one of the connection plates in adjacent another one of the pairs, at their ends in the longitudinal direction of the connection plates; and
   wherein an end portion of the other one of the connection plates in said each one of the pairs and an end portion of the other one of the connection plates in said another one of the pairs are bent in the radial direction so that these end portions are both apart from said one of the connection plates in said each one of the pairs, and said the other one of the connection plates in said each one of the pairs and said the other one of the connection plates in said another one of the pairs are serially connected to each other at their thus-bent portions, so that power is fed to the plurality of electromagnets.

2. The connection plates for power feeding of claim 1, wherein an intermediate fixation plate for fixing the connection plates in said each one of the pairs is placed in a side that is opposite, in a longitudinal direction of the connection plates in said each one of the pairs, to a portion where the connection plate therein is serially connected, and a clamping plate for clamping the connection plates in said another one of the pairs is placed in a side that is opposite, in a longitudinal direction of the connection plates in said another one of the pairs, to a portion where the connection plate therein is serially connected, so that the connection plates for power feeding are placed at a position higher than an installation base level at which the plurality of electromagnets is installed.

3. The connection plates for power feeding of claim 1, wherein the connection plates include end portions that are each bent in an L-shape, and are connected at each of the end portions to an electromagnet connection part that is a connection end of each of the electromagnets.

4. The connection plates for power feeding of claim 2, wherein the connection plates include end portions that are each bent in an L-shape, and are connected at each of the end portions to an electromagnet connection part that is a connection end of each of the electromagnets.

* * * * *